United States Patent
Teshigawara

(10) Patent No.: US 10,359,519 B2
(45) Date of Patent: Jul. 23, 2019

(54) NUCLEAR MEDICINE DIAGNOSTIC APPARATUS AND CALIBRATION METHOD

(71) Applicant: Canon Medical Systems Corporation, Otawara-shi (JP)

(72) Inventor: Manabu Teshigawara, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 0 days.

(21) Appl. No.: 15/865,504

(22) Filed: Jan. 9, 2018

(65) Prior Publication Data
US 2018/0196144 A1    Jul. 12, 2018

(30) Foreign Application Priority Data

Jan. 11, 2017    (JP) ................... 2017-002572

(51) Int. Cl.
| | | |
|---|---|---|
| G01T 1/16 | (2006.01) | |
| G01T 1/164 | (2006.01) | |
| A61B 6/03 | (2006.01) | |
| G01T 1/29 | (2006.01) | |
| A61B 6/00 | (2006.01) | |

(52) U.S. Cl.
CPC ............ *G01T 1/1642* (2013.01); *A61B 6/037* (2013.01); *G01T 1/1644* (2013.01); *G01T 1/1647* (2013.01); *A61B 6/032* (2013.01); *A61B 6/5205* (2013.01); *A61B 6/583* (2013.01); *G01T 1/2985* (2013.01)

(58) Field of Classification Search
CPC ...... G01T 1/1642; G01T 1/1644; A61B 6/037
See application file for complete search history.

(56) References Cited

U.S. PATENT DOCUMENTS

| | | | |
|---|---|---|---|
| 2004/0227091 A1 | 11/2004 | Leblanc et al. | |
| 2006/0054828 A1* | 3/2006 | Fritzler | G01T 1/2018 250/370.1 |
| 2009/0159804 A1* | 6/2009 | Shibuya | G01T 1/2985 250/363.03 |

(Continued)

FOREIGN PATENT DOCUMENTS

| | | |
|---|---|---|
| JP | 2004-340968 | 12/2004 |
| JP | 2011-149883 | 8/2011 |
| WO | WO 2010/041313 A1 | 4/2010 |

*Primary Examiner* — Hugh Maupin
(74) *Attorney, Agent, or Firm* — Oblon, McClelland, Maier & Neustadt, L.L.P.

(57) ABSTRACT

A nuclear medicine diagnostic apparatus according to an embodiment includes a scintillator configured to be formed of a single crystal and convert a gamma ray into light; a plurality of photodetectors configured to be arranged on different faces or tangents of the scintillator and each of which is configured to output an electric signal in response to incidence of the light resulting from the converting by the scintillator; storage circuitry configured to store, in advance, correspondence information in which each position in the scintillator is associated with a first intensity distribution indicating intensities of the electric signals that are output by the respective photodetectors; and specifying circuitry configured to specify a conversion position in which the gamma ray that is emitted from the subject is converted into the light in the scintillator by using the correspondence information and a second intensity distribution indicating the intensities of the electric signals.

16 Claims, 11 Drawing Sheets

(56) References Cited

U.S. PATENT DOCUMENTS

2010/0102215 A1\* 4/2010 Liang ..................... G01T 1/00
                                                   250/252.1
2011/0101229 A1   5/2011 Inadama et al.

\* cited by examiner

| MODULE ID | SPATIAL POSITION (P) | ENERGY VALUE (E) | DETECTION TIME (T) |
|---|---|---|---|
| D1 | P11 | E11 | T11 |
|  | P12 | E12 | T12 |
|  | P13 | E13 | T13 |
|  | ⋮ | ⋮ | ⋮ |

| MODULE ID | SPATIAL POSITION (P) | ENERGY VALUE (E) | DETECTION TIME (T) |
|---|---|---|---|
| D2 | P21 | E21 | T21 |
|  | P22 | E22 | T22 |
|  | P23 | E23 | T23 |
|  | ⋮ | ⋮ | ⋮ |

| MODULE ID | SPATIAL POSITION (P) | ENERGY VALUE (E) | DETECTION TIME (T) |
|---|---|---|---|
| D3 | P31 | E31 | T31 |
|  | P32 | E32 | T32 |
|  | P33 | E33 | T33 |
|  | ⋮ | ⋮ | ⋮ |

| COINCIDENCE NO. | SPATIAL POSITION (P) | ENERGY VALUE (E) | DETECTION TIME (T) | SPATIAL POSITION (P) | ENERGY VALUE (E) | DETECTION TIME (T) |
|---|---|---|---|---|---|---|
| 1 | P11 | E11 | T11 | P22 | E22 | T22 |
| 2 | P12 | E12 | T12 | P32 | E32 | T32 |
| 3 | P13 | E13 | T13 | P33 | E33 | T33 |
| ... | ... | ... | ... | ... | ... | ... |

FIG.8
| SPATIAL POSITION (P) | FIRST INTENSITY DISTRIBUTION |
|---|---|
| (x1, y1, z1) | 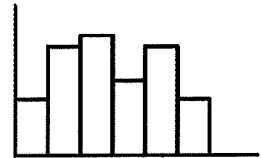 |
| (x1, y2, z1) | 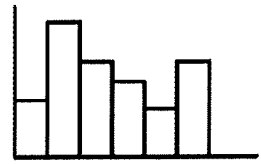 |
| (x1, y3, z1) | 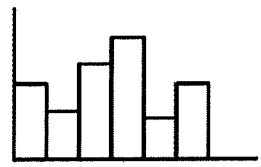 |
| ... | ... |
| (x2, y1, z1) | 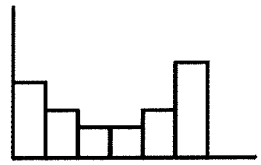 |
| ... | ... |
| (x1, y1, z2) |  |
| ... | ... |

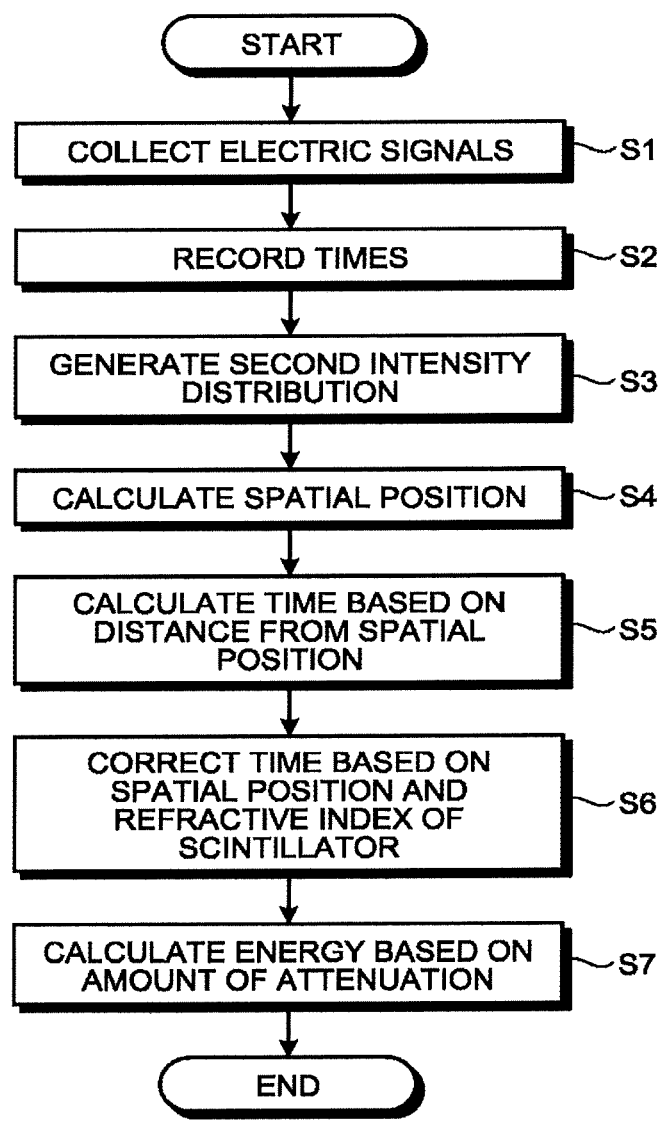

NUCLEAR MEDICINE DIAGNOSTIC APPARATUS AND CALIBRATION METHOD

CROSS-REFERENCE TO RELATED APPLICATIONS

This application is based upon and claims the benefit of priority from Japanese Patent Application No. 2017-002572, filed on Jan. 11, 2017; the entire contents of which are incorporated herein by reference.

FIELD

Embodiments descried herein relate generally to a nuclear medicine diagnostic apparatus and a calibration method.

BACKGROUND

In general, a gamma ray detector (hereinafter, "detector") in a positron emission computed tomography (PET) apparatus receives, with a photomultiplier, scintillation light (scintillation photons or optical photons) emitted when a gamma ray emitted from a subject is incident on a scintillator and converts the scintillation light into electronic signals.

For a conventional detector in a PET apparatus, for example, a detector consisting of a large number of scintillator crystals arrayed and each sized as a unit at a depth of 4 mm, a width of 4 mm, and a height (thickness) of 20 mm is used. A reflective member is interposed between scintillator crystals and is structured to prevent scintillation light occurring in one scintillation crystal from leaking to the surrounding scintillator crystals (to prevent crosstalk). For this reason, the conventional detector discretely identifies in which scintillator crystals scintillation events occur and identifies coincidence counting and line-of-response (LOR) on the basis of the results of the identifying.

A PET apparatus having a depth-of-interaction (COI) detection function has the same system where a detector discretely identifies scintillation events. Regardless in which position in a scintillator crystal a scintillation event occurs, such a conventional PET apparatus identifies the scintillation event as one occurring in a single scintillator crystal in a finite size. For this reason, the form of expression of the position in which the identified scintillation event occurs serves as the main item that gives a limit on the spatial resolution and the time resolution.

BRIEF DESCRIPTION OF THE DRAWINGS

FIG. 6 is a diagram for explaining a chronological list of coincidence counting information in the first embodiment;

FIG. 8 is a diagram for explaining correspondence information in the first embodiment;

FIG. 12 is a flowchart illustrating a process procedure of calculating counting information performed by a PET apparatus according to the first embodiment.

DETAILED DESCRIPTION

A nuclear medicine diagnostic apparatus and a calibration method according to an embodiment will be described below with reference to the accompanying drawings. An exemplary case where the nuclear medicine diagnostic apparatus is a positron emission computed tomography (PET) apparatus will be described below. The embodiments are not limited to the following embodiment. The content of descriptions of one embodiment is in principle applicable similarly to other embodiments.

A nuclear medicine diagnostic apparatus according to an embodiment includes a scintillator configured to be formed of a single crystal and convert a gamma ray into light; a plurality of photodetectors configured to be arranged on different faces or tangents of the scintillator and each of which is configured to output an electric signal in response to incidence of the light resulting from the converting by the scintillator; storage circuitry configured to store, in advance, correspondence information in which each position in the scintillator is associated with a first intensity distribution indicating intensities of the electric signals that are output by the respective photodetectors; and specifying circuitry configured to specify a conversion position in which the gamma ray that is emitted from the subject is converted into the light in the scintillator by using the correspondence information and a second intensity distribution indicating the intensities of the electric signals that are output by the respective photodetectors that detect the light originating from the gamma ray emitted from a subject and converted in the scintillator.

First Embodiment

Figure 1:
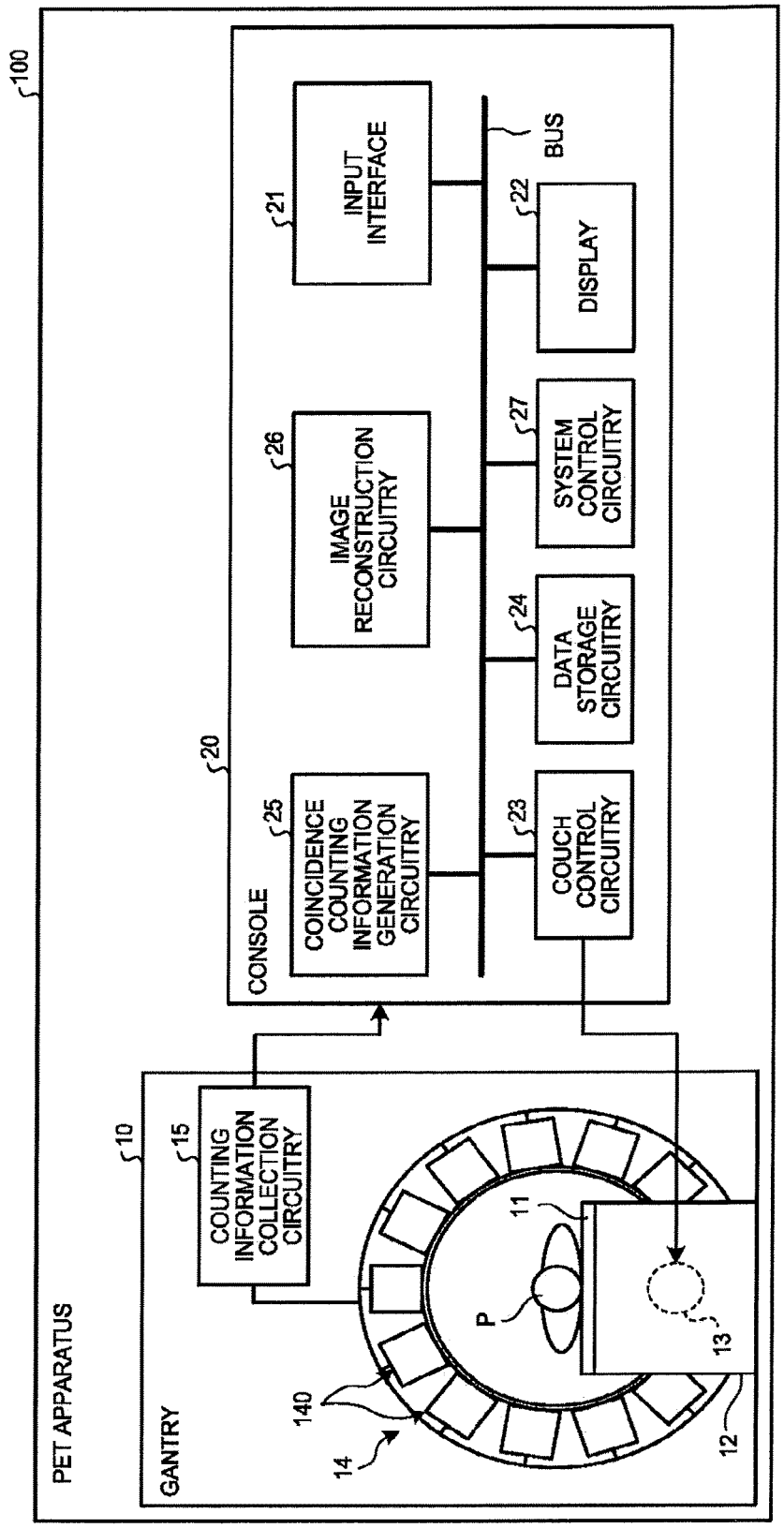
FIG. 1 is a block diagram illustrating a configuration of a PET apparatus according to a first embodiment.

FIG. 1 is a block diagram illustrating a configuration of a PET apparatus 100 according to a first embodiment. As illustrated in FIG. 1, the PET apparatus 100 according to the first embodiment includes a gantry 10 and a console 20.

The gantry 10 detects a pair of annihilation gamma rays that are emitted from a positron in a subject P with a detector that is arranged such that the detector circularly surrounds the subject P, generates counting information from output signals from the detector, and collects the counting information. As illustrated in FIG. 1, the gantry 10 includes a couch top 11, a couch 12, a couch driver 13, a detector 14 and counting information collection circuitry 15. As illustrated in FIG. 1, the gantry 10 has a hollow serving as an imaging port.

The couch top 11 is a bed on which the patient P is placed. The couch top 11 is arranged on the couch 12. The couch driver 13 moves the couch top 11 under the control of couch control circuitry 23, which will be described below. For example, the couch driver 13 moves the subject P into the imaging port of the gantry 10 by moving the couch top 11.

The detector 14 detects annihilation gamma rays that are emitted from a positron in the subject P. For example, as illustrated in FIG. 1, the detector 14 includes a plurality of detector modules 140 that are arranged such that the detector modules 140 circularly surround the subject P. FIG. 1 exemplifies the case where the detector modules 140 are arranged in the directions of tangents to the circumference of the detector 14. Alternatively, the detector modules 140 may be arranged in the direction of the body-axis of the subject P.

Figure 2:
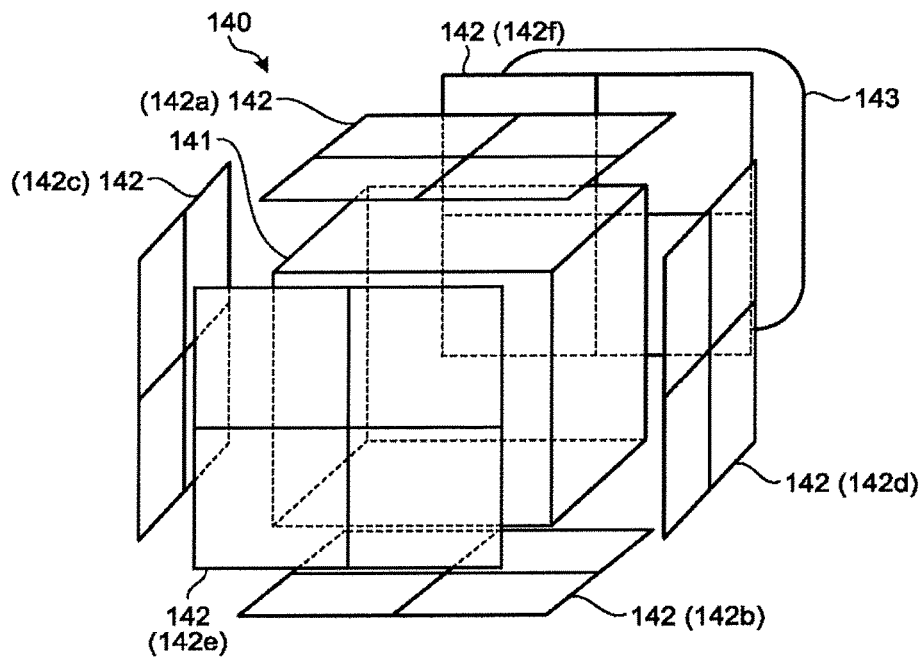
FIG. 2 is a diagram for explaining a detector module according to the first embodiment.

FIG. 2 is a diagram for explaining the detector module 140 according to the first embodiment. As illustrated in FIG. 2, the detector module 140 is an Anger-type detector employing a photon counting method and the detector module 140 includes a scintillator 141, a plurality of silicon photomultiplier (SiPM) panels 142, and counting information calculation circuitry 143. To distinguish the SiPM panels 142 from one another, for convenience of descriptions, the SiPM panels 142 are denoted with different reference numbers that are a SiPM panel 142a, a SiPM panel 142b, a SiPM panel 142c, a SiPM panel 142d, a SiPM panel 142e and a SiPM panel 142f and are described.

The scintillator 141 is configured monolithically, that is, uniformly or in a solid piece. In other words, for the scintillator 141 configured monolithically, for example, a large number of scintillator crystals arrayed and each serving as a unit are not used but a single uniform scintillator crystal without being compartmented is used. For this reason, no reflective member is interposed in the scintillator 141.

As illustrated in FIG. 2, the scintillator 141 is a hexahedron. FIG. 2 illustrates the case where the scintillator 141 is a cube. Alternatively, the scintillator 141 may be a rectangular cuboid. The scintillator 141 is formed of a scintillator crystal suitable for the TOF, such as Lutetium Yttrium Oxyorthosilicate (LYSO), Lutetium Oxyorthosilicate (LSO), and Lutetium Gadolinum Oxyorthosilicate to (LGSO).

The scintillator 141, for example, converts an annihilation gamma ray emitted from a positron in the subject P into scintillation light (scintillation photons or optical photons). In sum, the scintillator 141 is configured monolithically and converts a gamma ray into scintillation light.

The SiPM panels 142 are arranged in different positions in the scintillator 141. The SiPM panels 142 detect the scintillation light resulting from the conversion by the scintillator 141 and generate electric signals. The SiPM panels 142 are provided on at least two of the faces of the scintillator 141.

For example, as illustrated in FIG. 2, the SiPM panels 142 are provided on the six faces of the scintillator 141. In other words, all the six faces of the monolithically-configured scintillator 141 are covered with the SiPM panels 142. The number of faces of the scintillator 141 to be covered may be smaller than six or part of all the faces may be covered. The larger the ratio of the surface of the scintillator 141 covered with the SiPM panels 142 to the entire surface of the scintillator 141 is, the more the S/N of the output signal improves.

The SiPM panels 142 may be formed on a substrate and then arranged on the scintillator 141. In other words, the SiPM panels 142 may be optically attached to the scintillator 141. Alternatively, the SiPM panels 142 may be formed directly on the scintillator 141. In other words, the SiPM panels 142 may be formed directly on the surface of the scintillator 141 as a semiconductor.

Each of the SiPM panels 142 includes SiPMs each serving as a channel. For example, FIG. 2 exemplifies the case where each of the SiPM panels 142 covering the respective faces of the scintillator 141 includes four (=2×2) SiPMs. Alternatively, the number of SiPMs per face of which the SiPM panel 142 consists of may be one (=1×1) or may be 32 (=8×4). When the number of SiPMs is four, the total number of output channels of the detector module 140 is 24 (=2×2×6 faces). Each of the SiPMs is an exemplary photodetector.

The counting information calculation circuitry 143 includes a clock circuit, a trigger circuit, an energy integral circuit, and an input/output circuit with respect to the outside. The counting information calculation circuitry 143 is an electronic circuit having a function of processing signals from the SiPM panels 142 and outputting the processing result to the counting information collection circuitry 15.

Figure 3:
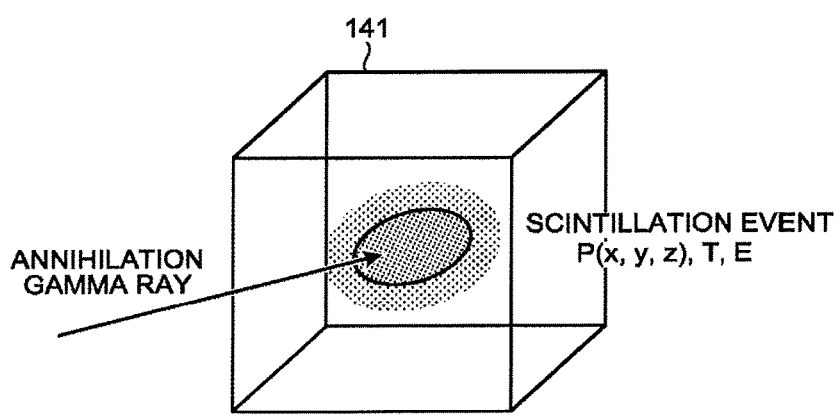
FIG. 3 is a diagram for explaining counting information collection circuitry according to the first embodiment.

The counting information collection circuitry 15 is an electronic circuit having a function of collecting the processing results that are output by the respective counting information calculation circuitry 143 and calculating counting information. The counting information collection circuitry 15 is an exemplary specifying circuitry. FIG. 3 is a diagram for explaining the counting information collection circuitry 15 according to the first embodiment.

FIG. 3 illustrates only the scintillator 141 for convenience of descriptions. An annihilation gamma ray is incident as illustrated in FIG. 2 and then the counting information collection circuitry 15 calculates, as counting information, a spatial position (P) at the time of conversion of the annihilation gamma ray into scintillation light in the scintillator 141, a time (T) at which the annihilation gamma ray is converted, and an energy value (E) of the converted gamma ray. The counting information collection circuitry 15 stores the collected counting information in data storage circuitry 24, which will be described below. Details of the process of calculating counting information performed by the counting information collection circuitry 15 will be described in details below. The time (T) of the conversion is also referred to as a detection time (T).

The console accepts an operation on the PET apparatus 100 by the operator, controls PET image capturing, and reconstructs a PET image by using the counting information collected by the gantry 10. As illustrated in FIG. 1, the console 20 includes an input interface 21, a display 22, the couch control circuitry 23, the data storage circuitry 24, coincidence counting information generation circuitry 25, image reconstruction circuitry 26, and system control circuitry 27. The components of the console 20 are connected with one another via a bus.

The input interface 21 includes a mouse and a keyboard that are used by the operator of the PET apparatus 100 to input various types of instructions and various types of setting. The input interface 21 transfers the various types of instructions and various types of settings, which are input, to the system control circuitry 27. The display 22 is, for example, a monitor that is referred to by the operator. Under the control of the system control circuitry 27, the display 22 displays a breathing waveform of the subject P and a PET image and displays a graphical interface (GUI) for accepting various types of instructions and various types of setting from the operator. The couch control circuitry 23 is an electronic circuit having a function of controlling the couch driver 13.

Figures 4, 5:
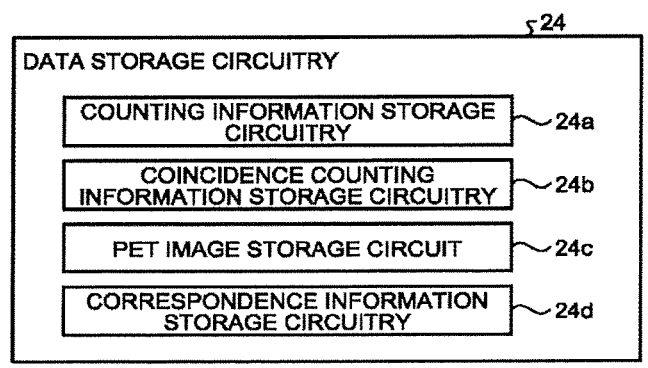
FIG. 4 is a diagram for explaining data storage circuitry according to the first embodiment.
FIG. 5 is a diagram for explaining lists of counting information in the first embodiment.

The data storage circuitry 24 is an electronic circuit having a function of storing various types of data used in the PET apparatus 100. FIG. 4 is a diagram for explaining the data storage circuitry 24 according to the first embodiment. As illustrated in FIG. 4, the data storage circuitry 24 includes counting information storage circuitry 24a, coincidence counting information storage circuitry 24b, PET image storage circuitry 24c and correspondence information storage circuitry 24d. The data storage circuitry 24 is implemented with, for example, a semiconductor memory device, such as a random access memory (RAM) or a flash memory, a hard disk, or an optical disk.

The counting information storage circuitry 24a is an electronic circuit having a function of storing a list of the sets of counting information that are collected by the counting information collection circuitry 15. The counting information list stored in the counting information storage circuitry 24a is used for processing performed by the coincidence counting information generation circuitry 25. The counting information list stored in the counting information storage circuitry 24a may be deleted after being used for the processing performed by the coincidence counting information generation circuitry 25 or may be stored for given period.

FIG. 5 is a diagram for explaining the counting information list in the first embodiment. As illustrated in FIG. 5, the counting information storage circuitry 24a stores counting information containing the spatial position (P), the energy value (E) and the detection time (T) in association with the module ID that identifies the detector module 140.

The coincidence counting information storage circuitry 24b is an electronic circuit having a function of storing a chronological list of sets of coincidence counting information that are generated by the coincidence counting information generation circuitry 25. The chronological list of sets of coincidence counting information stored by the coincidence counting information storage circuitry 24b is used for processing performed by the image reconstruction circuitry 26. The chronological list of the coincidence counting information stored in the coincidence counting information storage circuitry 24b may be deleted after being used for the processing performed by the image reconstruction circuitry 26 or may be stored for a given period.

FIG. 6 is a diagram for explaining the chronological list of the coincidence counting information in the first embodiment. As illustrated in FIG. 6, the coincidence counting information storage circuitry 24b stores pairs of counting information each in association with a coincidence number that is a serial number of coincidence counting information. Sets of information stored as one pair of the same coincidence number represent that the time difference between detection times (T) is within a time window width. In other words, the example illustrated in FIG. 6 indicates that T11 and T22 corresponding to the coincidence No. 1 are within the time window width, T12 and T32 corresponding to the coincidence No. 2 are within the time window width, and T13 and T33 corresponding to the coincidence No. 3 are within the time window width. In the first embodiment, the chronological list of the coincidence counting information has an approximately chronological order based on the times (T) at each of which counting information is detected.

The PET image storage circuitry 24c is an electronic circuit having a function of storing a PET image that is reconstructed by the image reconstruction circuitry 26. The PET image that is stored in the PET image storage circuitry 24c is displayed by the system control circuitry 27 on the display 22.

The correspondence information storage circuitry 24d is an electronic circuit having a function of storing correspondence information that is generated by the system control circuitry 27. For example, the correspondence information storage circuitry 24d stores correspondence information in which each position in the scintillator 141 is associated with a first intensity distribution indicating the intensities of the electric signals that are output from the respective SiPMs in response to the incidence of light into which a gamma ray is converted in the position. Details of the correspondence information stored in the correspondence information storage circuitry 24d will be described below.

FIG. 1 will be referred back here. The coincidence counting information generation circuitry is an electronic circuit having a function of generating chronological list of sets of coincidence counting information by using the list of sets of counting information that are collected by the counting information collection circuitry 15. Specifically, the coincidence counting information generation circuitry searches for pairs of sets of counting information each about approximately simultaneous counting of a pair of annihilation gamma rays from the counting information lists stored in the counting information storage circuitry 24a on the basis of the times (T) at each of which counting information is detected. The coincidence counting information generation circuitry 25 generates coincidence counting information about each of the searched pairs of sets of counting information and stores the generated sets of coincidence counting information in the coincidence counting information storage circuitry 24b while arranging the generated sets of coincidence counting information roughly chronologically.

For example, the coincidence counting information generation circuitry 25 is an electronic circuit having a function of generating coincidence counting information according to a coincidence counting information generation condition that is input by the operator. A time window width is specified as the coincidence counting information generation condition. For example, the coincidence counting information generation circuitry 25 generates coincidence counting information according to the time window width.

For example, the coincidence counting information generation circuitry 25 refers to the counting information storage circuitry 24a and searches for a pair of sets of counting information whose difference between the detection times (T) is within the time window width among the detector modules 140. For example, when the coincidence counting information generation circuitry 25 searches for a pair of "P11, E11 and T11" and "P22, E22 and T22" as a pair satisfying the coincidence counting information generation condition, the coincidence counting information generation circuitry 25 generates the pair as coincidence counting information and stores the coincidence counting information in the coincidence counting information storage circuitry 24b. The coincidence counting information generation circuitry may generate coincidence counting information by using an energy window width in addition to the time window width.

The image reconstruction circuitry 26 is an electronic circuit having a function of reconstructing a PET image. Specifically, the image reconstruction circuitry 26 reads the chronological list of the coincidence counting information stored in the coincidence counting information storage circuitry 24b and reconstructs a PET image by using the read chronological list. The image reconstruction circuitry 26 stores the reconstructed PET image in the PET image storage circuitry 24c.

The system control circuitry 27 is an electronic circuit having a function of controlling the entire PET apparatus 100 by controlling the gantry 10 and the console 20. For example, the system control circuitry 27 controls imaging in the PET apparatus 100. The system control circuitry 27 generates correspondence information. Details of a correspondence information generation process performed by the system control circuitry 27 will be described below. The system control circuitry 27 is an exemplary calculation circuitry.

The above-described components, such as the couch control circuitry 23, the coincidence counting information generation circuitry 25, the image reconstruction circuitry 26 and the system control circuitry 27 are implemented with integrated circuits, such as an application specific integrated circuit (ASIC) and a field programmable gate array (FPGA), and electronic circuits, such as a central processing unit (CPU) and a micro processing unit (MPU).

The entire configuration of the PET apparatus 100 according to the first embodiment has been described. The PET apparatus according to the first embodiment having the configuration calculates, as counting information, a spatial position (P) in which an annihilation gamma ray that is incident is converted into scintillation light in the scintillator 141, a time (T) of the conversion, and an energy value (E) of the converted gamma ray. The PET apparatus 100 then generates a chronological list of sets of coincidence counting information by using the lists of the calculated counting information and reconstructs a PET image by using the chronological list. The process of calculating counting information will be described below.

First of all, a process of calculating counting information will be described. The counting information calculation circuitry 143 collects electric signals that are output from the SiPMs of each of the SiPM panels 142. The counting information calculation circuitry 143 records the times at each of which an electric signal is collected.

Figure 7:
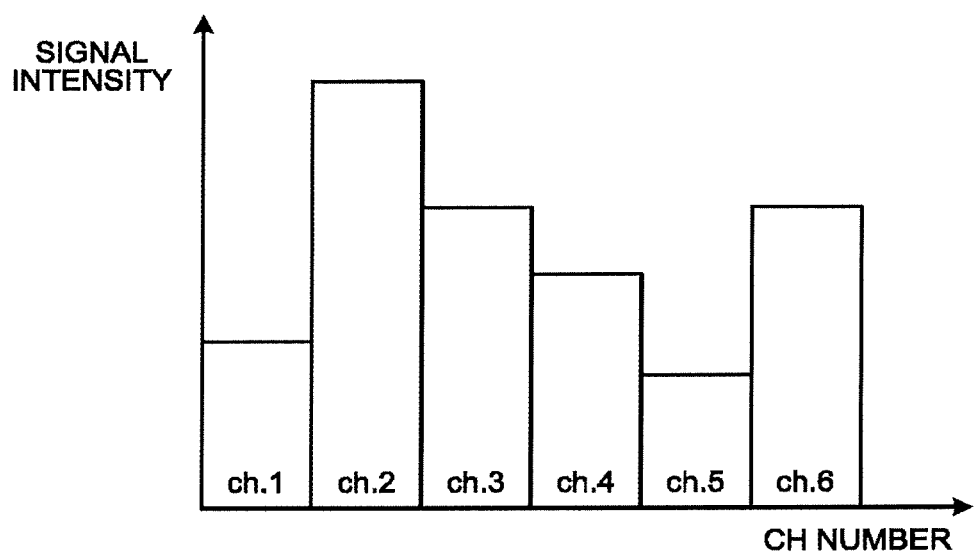
FIG. 7 is a diagram illustrating an exemplary second intensity distribution according to the first embodiment.

The counting information calculation circuitry 143 generates a second intensity distribution indicating the intensities of the electronic signals that are output by the respective SiPMs each of which detects light originating from the gamma ray that is emitted from the subject P and that is converted in the scintillator 141. The counting information calculation circuitry 143 generates a histogram as the second intensity distribution. FIG. 7 is a diagram illustrating an exemplary second intensity distribution according to the first embodiment.

The horizontal axis in FIG. 7 indicates channel numbers and the vertical axis in FIG. 7 indicates signal intensities of the respective channels. The example illustrated in FIG. 7 illustrates the case where the number of SiPMs per face forming the SiPM panel 142 is one and the number of channels is 6. The example illustrated in FIG. 7 represents signal intensities from that of the channel number 1 (ch. 1) to that of the channel number 6 (ch. 6) sequentially from the left side of the horizontal axis. In the example illustrated in FIG. 7, the signal intensity represented by the vertical axis is a value obtained by performing integral calculation on the intensities of the electric signals from the respective SiPMs. The counting information calculation circuitry 143 generates a histogram like that illustrated in FIG. 7 with respect to each scintillation event. The counting information calculation circuitry 143 outputs the times at which the electric signals are acquired and the generated histogram to the counting information collection circuitry 15.

The counting information collection circuitry 15 specifies a conversion position in which the gamma ray emitted from the subject P is converted into light in the scintillator 141 by using the second intensity distribution generated by the counting information calculation circuitry 143 and the correspondence information.

Before the operations performed by the counting information collection circuitry 15 to specify a conversion position are described, details of the correspondence information stored in the correspondence information storage circuitry 24d will be described. FIG. 8 is a diagram for explaining the correspondence information in the first embodiment. As illustrated in FIG. 8, the correspondence information storage circuitry 24d stores the first intensity distributions in association with the spatial positions (P), respectively.

The correspondence information storage circuitry 24d stores sets of three-dimensional coordinates represented by, for example, (x1,y1,z1), (x1,y2,z1), (x1,y3,z1), (x2,y1,z1), and (x1,y1,z2) as spatial positions (P). The correspondence information storage circuitry 24d generates a histogram as a first intensity distribution. The histograms stored as the first intensity distributions by the correspondence information storage circuitry 24d are the same as that illustrated in FIG. 7. In other words, the example illustrated in FIG. 8 represents the case where the number of channels is 6. The example illustrated in FIG. 8 represents the signal intensities from that of the channel number 1 (ch. 1) to that of the channel number 6 (ch. 6) sequentially from the left side of the horizontal axis. In the example illustrated in FIG. 8, each of the signal intensities indicated by the vertical axis is a value obtained by performing integral calculation on the intensities of the electric signals from each channel.

The counting information collection circuitry 15 specifies a conversion position in which a gamma ray emitted from the subject P is converted into light in the scintillator 141 by using the correspondence information illustrated in FIG. 8. For example, the counting information collection circuitry 15 calculates similarity between the first intensity distribution and the second intensity distribution and, based on the calculated similarity, specifies a conversion position. For example, the counting information collection circuitry 15 calculates similarity between the second intensity distribution illustrated in FIG. 7 and the first intensity distribution illustrated in FIG. 8. In the correspondence information illustrated in FIG. 8, the first intensity distribution with respect to the spatial position (P) corresponding to (x1,y2,z1) approximately matches the second intensity distribution illustrated in FIG. 7. In other words, the shape of the first intensity distribution illustrated in FIG. 8 where the spatial position (P) corresponds to (x1,y2,z1) approximately match the shape of the second intensity distribution in FIG. 7. In this case, the counting information collection circuitry 15 specifies that, in a scintillation event that causes generation of the histogram illustrated in FIG. 7, the incident annihilation gamma ray is converted into light in the spatial position (P) at (x1,y2,z1) the scintillator 141. In other words, in the case of the light scintillation event that causes generation of the histogram illustrated in FIG. 7, the counting information collection circuitry 15 specifies that the conversion position of the conversion into light in the scintillator 141 is (x1,y2,z1).

The counting information collection circuitry 15 further specifies a time of conversion into scintillation light in the scintillator 141 on the basis the distances from the conversion position to the SiPMs. For example, the counting information collection circuitry 15 calculates a time (T) of conversion into scintillation light in the scintillator 141 on the basis of the distances from the spatial position (P) to the SiPMs. For example, the counting information collection circuitry 15 specifies times at each of which an electric signal is acquired from each of the channels as pre-correction detection times (T'). More specifically, the counting information collection circuitry 15 specifies a pre-correction detection time (T') at an accuracy of a unit of $10^{-12}$ seconds (Pico seconds). The pre-correction detection time (T') may be an absolute time that is recorded by the clock circuit or may be the elapse of time from the imaging start time point.

The pre-correction detection times (T') are times at each of which the counting information calculation circuitry 143 acquires an electronic signal from a SiPM and is not the time (T) of conversion into scintillation light in the scintillator 141. In other words, each of the pre-correction detection times (T') is a time that is behind the detection time (T) at which the annihilation gamma ray is converted into the scintillation light in the scintillator 141 and that corresponds to the distance by which the scintillation light travels until the scintillation light is received by the SiPM. The counting information collection circuitry 15 corrects the pre-correction detection times (T') on the basis of the distances from the spatial position (P) to the SiPMs and calculates the time (T) of conversion into the scintillation light. The counting information collection circuitry 15 may perform collation with a time-digital-converter (TDC) circuit for highly accurate time measurement.

A gamma ray that is incident on the scintillator 141 is not influenced by the refractive index of the scintillator 141; however, the light resulting from the conversion in the scintillator 141 is influenced by the refractive index of the scintillator 141. For example, when N denotes a refractive index, the velocity of light is 1/N times. Based on the specified conversion position and the refractive index of the scintillator 141, the counting information collection circuitry 15 further corrects the time.

The counting information collection circuitry 15 specifies the energy value of the gamma ray converted into the scintillation light in the scintillator 141 on the basis of an amount of attenuation from the conversion position to the SiPM. For example, the counting information collection circuitry 15 calculates an energy value (E) based on the amount of attenuation from the spatial position (P) to the SiPM. For example, the counting information collection circuitry 15 specifies the pre-correction energy value (E') of the annihilation gamma ray incident on the detector module 140 by performing integral calculation on the intensities of the electronic signals that are output from the respective SiPMs.

The pre-correction energy value (E') is the integration of the intensities of the electronic signals at the time when the counting information calculation circuitry 143 acquires the electronic signals from the SiPMs and is not the energy value (E) of the annihilation gamma ray at the time of the conversion into the scintillation light. In other words, the pre-correction energy value (E') is an energy value of the scintillation light attenuated, during the travel until the reception of the scintillation light by the SiPMs, with respect to the energy value (E) of the annihilation gamma ray at the time when the annihilation gamma ray is converted into the scintillation light in the scintillator 141. For this reason, based on the amount of attenuation during the travel of the scintillation light from the spatial position (P) to the SiPMs, the counting information collection circuitry 15 corrects the pre-correction energy value (E') and calculates the energy value (E).

Figure 9:
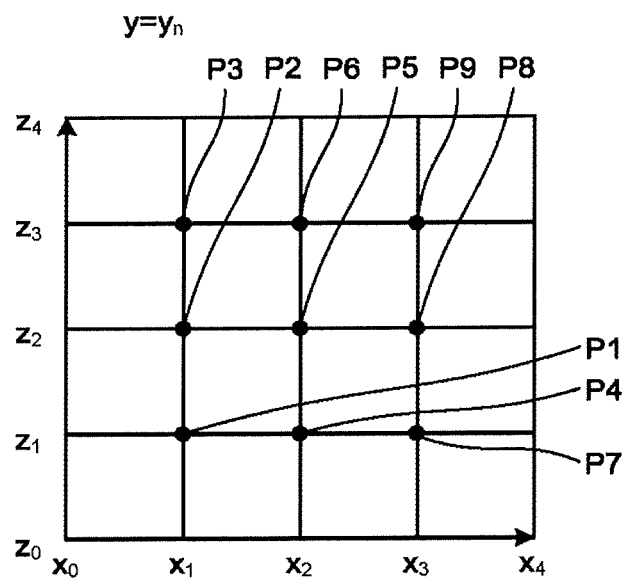
FIG. 9 is a diagram for explaining representative positions according to the first embodiment.

Subsequently, the process of generating correspondence information performed by the system control circuitry 27 will be described. The system control circuitry 27 calculates first intensity distributions corresponding respectively to positions in the scintillator 141 and stores the first intensity distributions in the correspondence information storage circuitry 24d. The system control circuitry 27 need not calculate first intensity distributions with respect to all positions in the scintillator 141. The system control circuitry 27 calculates first intensity distributions with respect to representative positions in the scintillator 141. FIG. 9 is a diagram for explaining representative positions according to the first embodiment.

FIG. 9 illustrates a z-x plane where the value of a y-coordinate in the scintillator 141 is $y_n$. For convenience of descriptions, FIG. 9 illustrates the case where representative positions P1 to P9 are set on the z-x plane where the value of a y-coordinate is $y_n$. Note that representative positions are set similarly on a z-x plane where the value of a y-coordinate is different from $y_n$. Any number of representative positions may be set.

Figure 10A:
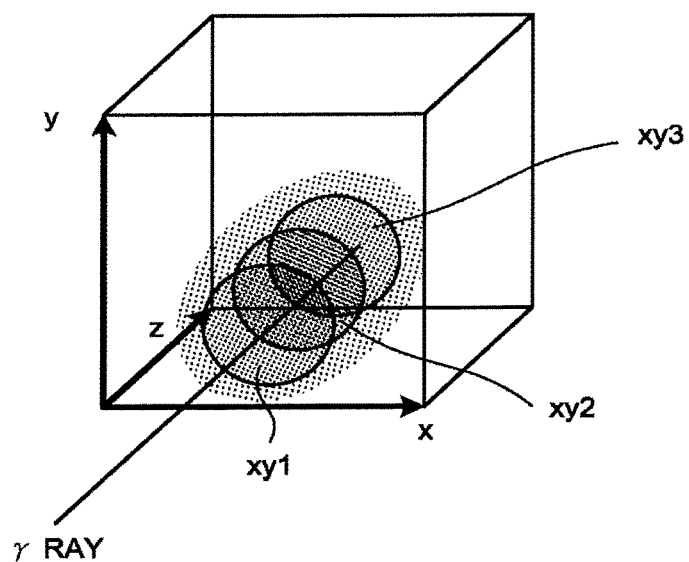
FIG. 10A is diagram for explaining a scintillation event of a gamma ray incident from a first direction according to the first embodiment.
Figure 10B:
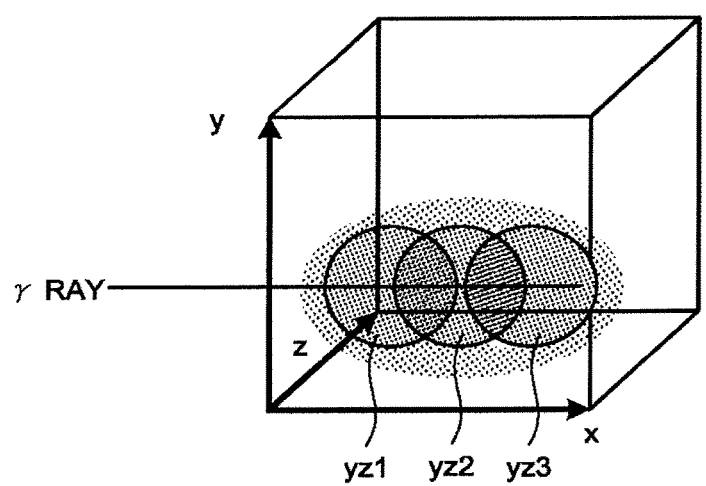
FIG. 10B is a diagram for explaining a scintillation event of a gamma ray incident from a second direction according to the first embodiment.

The case where a first intensity distribution with respect to P1 will be exemplified. In this case, two directions intersecting at the representative position P1 are set. For example, a direction passing through the P1 and parallel with the z-axis is set as a first direction and direction passing through P1 and parallel with the X-axis is set as a second direction. The system control circuitry 27 acquires third intensity distributions each indicating the intensities of the light incident on the scintillator 141 from the first direction and fourth intensity distributions each indicating the intensities of the light incident on the scintillator 141 from the second direction different from the first direction. FIG. 10A is a diagram for explaining a scintillation event of the gamma ray incident from the first direction according to the first embodiment. FIG. 10B is a diagram for explaining a scintillation event of the gamma ray incident from the second direction according to the first embodiment.

For example, as illustrated in FIG. 10A, the gamma ray is caused to be incident on the x-y plane of the scintillator 141 from that first direction that is a direction perpendicular to the x-y plane. More specifically, the gamma ray at 511 keV is caused to be incident on the x-y plane of the scintillator 141 with, for example, a pencil-type (cylindrical) radiation source in a direction perpendicular to the x-y plane in the Z-axis direction from the side of z0 to the size of z4. When a gamma ray is caused to be incident with, for example, a pencil-type (cylindrical) radiation source, it is preferable that no pile-up occur. The gamma ray incident on the scintillator 141 is converted into light in the scintillator 141. In the example illustrated in FIG. 10A, the gamma ray is converted into light at each of the positions xy1, xy2 and xy3. Each SiPM detects the light resulting from the conversion by the scintillator 141 and generates an electric signal.

For example, as illustrated in FIG. 10B, a gamma ray is caused to be incident on the y-z plane of the scintillator 141 from the second direction that is a direction perpendicular to the y-z plane. More specifically, a gamma ray at 511 keV is caused to be incident on the y-z plane of the scintillator 141 with, for example, a pencil-type (cylindrical) radiation source in a direction perpendicular to the y-z plane in the X-axis direction from the side of x0 to the side of x4. When a gamma ray is caused to be incident with, for example, a pencil-type (cylindrical) radiation source, it is also preferable that no pile-up occur. The gamma ray incident on the scintillator 141 is converted into light in the scintillator 141. In the example illustrated in FIG. 10B, the gamma ray is converted into light at each of the positions yz1, yz2 and yz3. Each SiPM detects the light resulting from the conversion by the scintillator 141 and generates an electric signal.

Figure 11A:
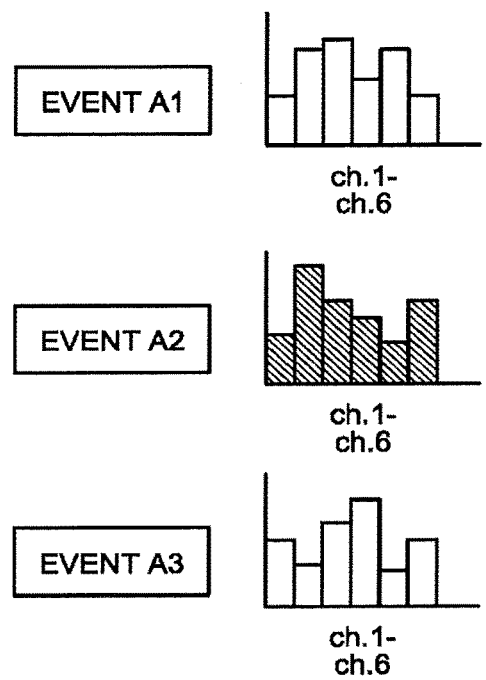
FIG. 11A is a diagram for explaining third intensity distributions according to the first embodiment.

Subsequently, the counting information calculation circuitry 143 acquires the electric signals that are generated by detecting the light incident on the scintillator 141 from the first direction from the respective SiPMs and generates the third intensity distributions each indicating the intensities of the electric signals that are output by the respective SiPMs. The counting information calculation circuitry 143 further acquires the electric signals that are generated by detecting the light incident on the scintillator 141 from the second direction from the respective SiPMs and generates the fourth intensity distributions each indicating the intensities of the electric signals that are output by the respective SiPMs. FIG. 11A is a diagram for explaining the third intensity distributions according to the first embodiment and 11B is a diagram for explaining the fourth intensity distributions according to the first embodiment.

Figure 11B:
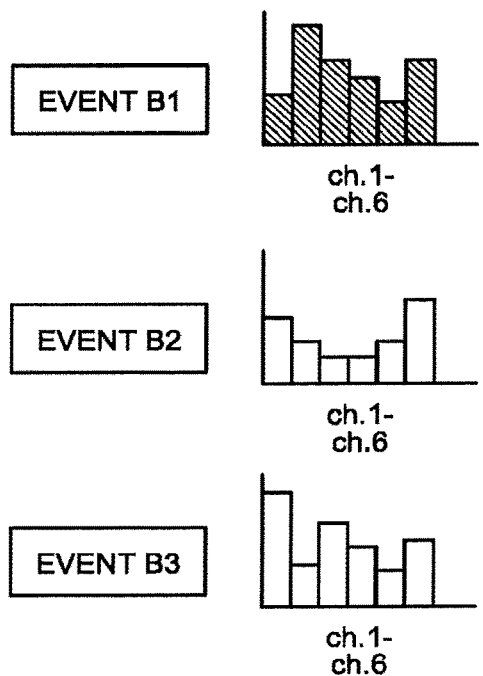
FIG. 11B is a diagram for explaining fourth intensity distributions according to the first embodiment.

For example, as illustrated in FIG. 11A, the counting information calculation circuitry 143 generates a histogram of an event A1, a histogram of an event A2, and a histogram of an event A3 as the third intensity distributions. As illustrated in FIG. 11B, the counting information calculation circuitry 143 generates a histogram of an event B1, a histogram of an event B2, and a histogram of an event B3 as the fourth intensity distributions.

The system control circuitry 27 calculates, as the first intensity distribution with respect to the position that is the intersection between the first direction and the second direction, an intensity distribution that is approximately identical between the third intensity distributions each indicating the intensities of the light incident on the scintillator 141 from the first direction and the fourth distribution distributions each indicating the intensities of the light incident on the scintillator 141 from the second direction are approximately the same. In the case illustrated in FIGS. 11A and 11E, the system control circuitry 27 determines that the histogram of the event A2 and the histogram of the event B1 are approximately identical and specifies the histograms as the first intensity distribution with respect to P1 that is the intersection between the first direction and the second direction. In other words, the system control circuitry 27 specifies the fourth intensity distribution having a shape approximately identical with that of the third intensity distribution as the first intensity distribution with respect to P1. The system control circuitry 27 then stores the representative position P1 and the determined first intensity distribution in association with each other in the correspondence information storage circuitry 24d.

In the same manner, the system control circuitry 27 specifies the first distribution distributions with respect to other representative positions the z-x plane where the value of a y-coordinate is $y_n$ and stores the correspondence information in the correspondence information storage circuitry 24d. Furthermore, when the system control circuitry 27 specifies the first intensity distributions with respect to all the representative positions on the z-x plane where the value of a y-coordinate is $y_n$, in the same manner, the system control circuitry 27 specifies first intensity distributions of the representative positions on the z-x plane where the value of a y-coordinate is different from $y_n$ and stores correspondence information in the correspondence information storage circuitry 24d.

The case has been described where, for example, when the first intensity distribution with respect to the representative position P1 is specified, the direction perpendicular to the x-y plane of the scintillator 141 from the side of z0 to the side of z4 in the z-axis direction is the first direction and the direction perpendicular to the y-z plane of the scintillator 141 from the side of x0 to the side of x4 in the x-axis direction is the second direction. Alternatively, when the first intensity distribution with respect to the representative position P1 is specified, the direction perpendicular to the x-y plane of the scintillator 141 from the side of z4 to the side of z0 in the z-axis direction may be the first direction and the direction perpendicular to the y-z plane of the scintillator 141 from the side of x4 to the side of x0 in the x-axis direction may be the second direction. When the scintillator 141 is a cube, the system control circuitry 27 is able to reduce the amount of calculation to one-eight by using the symmetry.

FIG. 12 is a flowchart illustrating a process procedure of calculating counting information performed by the PET apparatus 100 according to the first embodiment. With reference to FIG. 12, which component corresponds to which step in the flowchart will be described. Steps S1 to S3 are steps implemented by the counting information calculation circuitry 143 and steps S4 to S7 are steps implemented by the counting information collection circuitry 15.

At step S1, the counting information calculation circuitry 143 collects electronic signals that are output from the SiPMs contained in each of the SiPM panels 142. At step S2, the counting information calculation circuitry 143 records the times at which the electric signals are acquired, respectively. At step S3, the counting information calculation circuitry 143 generates a histogram indicating the signal intensities of the respective channels by using the electric signals from the SiPMs contained in each of the SiPM panels 142.

At step S4, the counting information collection circuitry 15 calculates a spatial position. The counting information collection circuitry 15 calculates a set of spatial coordinates (x,y,z) as the spatial position (P) of conversion into scintillation light.

At step S5, the counting information collection circuitry 15 calculates a time based on the distance from the spatial position. For example, the counting information collection circuitry 15 specifies absolute times recorded by the clock circuit as the detection times (T) at which electric signals are acquired from the respective channels. The counting information collection circuitry 15 corrects the detection tunes (T') on the basis of the distances from the spatial position (P) to the SiPMs and calculates the time (T) of the conversion into the scintillation light. At step S6, the counting information collection circuitry 15 further corrects the time (T) of the conversion into the scintillation light on the basis of the spatial position (P) and the refractive index of the scintillator 141.

At step S7, the counting information collection circuitry 15 calculates an energy value based on an amount of attenuation. For example, by performing integral calculation on the intensities of the electric signals that are output from the respective SiPMs, the counting information collection circuitry 15 specifies a pre-correction energy value (E') of the annihilation gamma ray incident on the detector module 140. The counting information collection circuitry 15 then calculates an energy value (E) by correcting the pre-correction energy value (E') on the basis of the amount of attenuation during the travel of the scintillation light from the spatial position (P) to the SiPMs.

Figure 13:
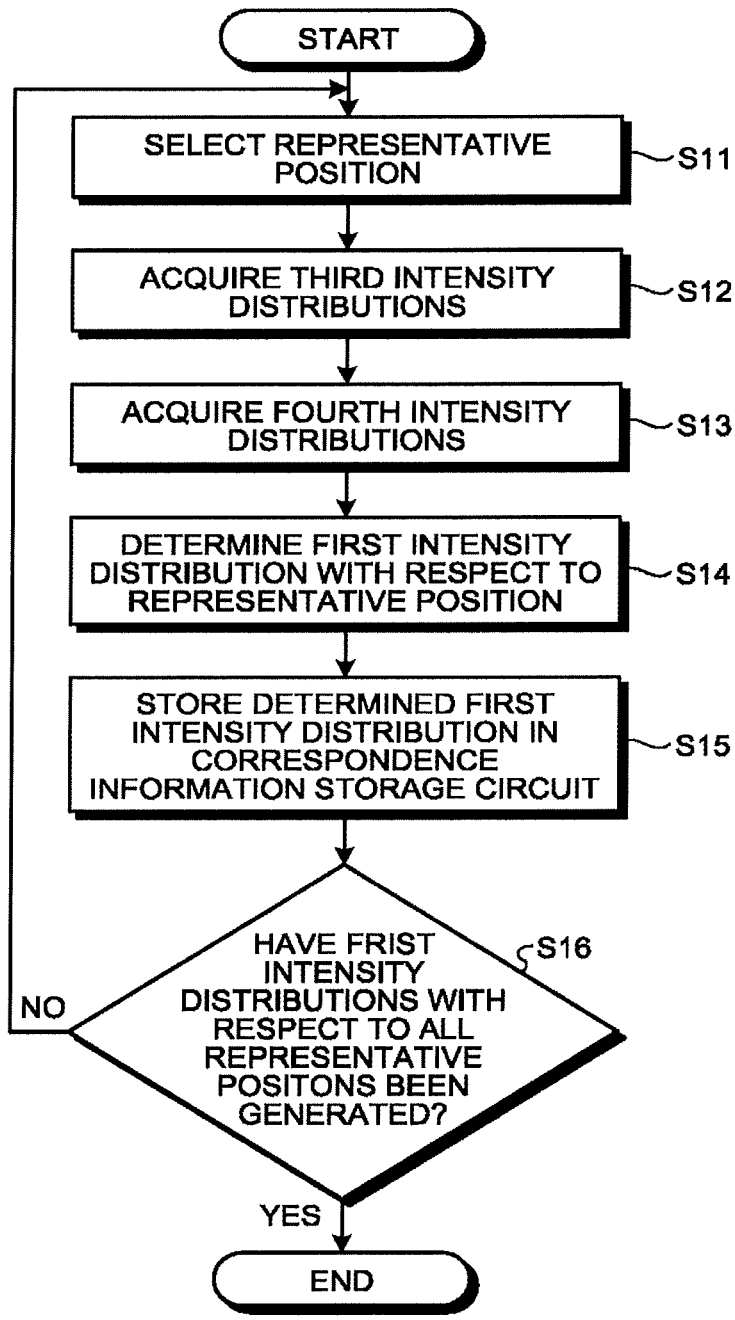
FIG. 13 is a flowchart illustrating a process procedure of generating correspondence information performed by the PET apparatus according to the first embodiment.

FIG. 13 is a flowchart illustrating a process procedure of generating correspondence information performed by the PET apparatus 100 according to the first embodiment. With reference to FIG. 13, which component corresponds to which step in the flowchart will be described. Steps S1 to step S16 are steps implemented by the system control circuitry 27.

At step S11, the system control circuitry 27 selects a representative position. For example, the system control circuitry 27 selects P1 among the representative positions illustrated in FIG. 9. At step S12, the system control circuitry 27 acquires third intensity distributions. In this case, for example, the counting information calculation circuitry 143 collects electric signals that are generated by the respective SiPMs by detecting the scintillation light generated by causing a gamma ray to be incident from the first direction with a pencil-type (cylindrical) radiation source. The counting information calculation circuitry 143 then generates third intensity distributions by using the collected electric signals. The system control circuitry 27, for example, acquires the third intensity distributions generated by the counting information calculation circuitry 143. For example, the system control circuitry 27 acquires the histogram of the event A1, the histogram of the event A2 and the histogram of the event A3, which are illustrated in FIG. 11A, as the third intensity distributions.

At step S13, the system control circuitry 27 acquires the fourth intensity distributions. In this case, for example, the counting information calculation circuitry 143 collects electric signals that are generated by the respective SiPMs by detecting scintillation light generated by causing a gamma ray to be incident from the second direction with a pencil-type (cylindrical) radiation source. The counting information calculation circuitry 143 then generates fourth intensity distributions by using the collected electric signals. The system control circuitry 27 acquires, for example, the fourth intensity distributions generated by the counting information calculation circuitry 143. For example, the system control circuitry 27 acquires the histogram of the event B1, the histogram of the event B2 and the histogram of the event B3, which are illustrated in FIG. 11B, as the fourth intensity distributions.

At step S14, the system control circuitry 27 determines the first intensity distribution of the representative position. For example, the system control circuitry 27 determines, as the first intensity distribution, an intensity distribution that is approximately identical between the third intensity distributions and the fourth intensity distributions.

At step S15, the system control circuitry 27 stores the determined first intensity distribution with respect to the representative position in the correspondence information storage circuitry 24d. For example, the system control circuitry 27 stores the representative position P1, which is selected at S11, and the first intensity distribution, which is determined at step S14, in association with each other in the correspondence information storage circuitry 24d.

At step S16, the system control circuitry 27 determines whether first intensity distributions with respect to all the representative positions have been determined. When it is determined that first intensity distributions with respect to all the representative positions have been determined (YES at step S16), the system control circuitry 27 ends the process of generating correspondence information.

On the other hand, when the system control circuitry does not determine that first intensity distributions with respect to all the representative positions have been determined (NO at step S16), the system control circuitry 27 moves to step S11.

In other words, the system control circuitry 27 repeatedly executes the process from step S11 to S15 until a new representative position is selected and first intensity distributions with respect to all the representative positions are determined.

As described above, in the detector module 140 according to the first embodiment, the scintillator 141 is configured monolithically. The SiPM panels 142 are arranged in different positions in the scintillator 141. For example, the SiPM panels 142 are arranged on at least two faces of the scintillator 141. The detector module 140 converts an annihilation gamma ray that is emitted from a positron in the subject P into scintillation light with the scintillator 141 that configured monolithically. The detector module 140 then converts the scintillation light resulting from the conversion into electric signals with the SiPM panels 142, processes the electric signals, and outputs the result of the processing to the counting information collection circuitry 15. The counting information calculation circuitry 143 generates a second intensity distribution indicating the intensities of the electric signals that are output by the respective SiPMs and outputs the second intensity distribution as the processing result to the counting information collection circuitry 15.

The counting information collection circuitry 15 collects the processing results that are output by the respective counting information calculation circuitry 143 and calculates counting information. The counting information collection circuitry 15 calculates counting information not as a discrete domain but as continuous values. For example, the counting information collection circuitry 15 specifies conversion positions in which the gamma ray emitted from the subject P is converted into light in the scintillator 141 by using the second intensity distribution and the correspondence information. In other words, the counting information collection circuitry 15 calculates a spatial position (P) representing a spatial position in the scintillator in which a scintillation event occurs by using real number (a floating point). Accordingly, according to the first embodiment, it is possible to specify an accurate position in which a gamma ray is converted into scintillation light. Accordingly, in the first embodiment, it is possible to remove a fundamental drag against improving the spatial resolution.

Not by identifying the scintillation in a discrete domain that is a limited breadth but by specifying the scintillation as continuous values, the counting information collection circuitry 15 corrects the time delays from the occurrence of the scintillation event until the reception of the scintillation light by the SiPM panels 142 and calculates the time (T) of conversion into scintillation light in a real number (a floating point) with respect to each scintillation event. Accordingly, according to the first embodiment, it is possible to increase the time resolution.

Not by identifying the scintillation as a discrete domain that is a limited spread but by specifying the scintillation as continuous values, the counting information collection circuitry 15 corrects the value that is the energy value attenuated during the travel of the scintillation light until the reception of the scintillation light by the SiPM and calculates the energy value (E) of the annihilation gamma ray in a real number (a floating point) with respect to each scintillation event. The counting information collection circuitry 15 uses the calculated counting information as input data for reconstructing an image and uses the real numbers (floating points) as list mode data. Accordingly, according to the first embodiment, it is possible to remove a drag against improving the spatial resolution and the time resolution. Furthermore, in the first embodiment, as the image reconstruction circuitry 26 reconstructs an image from the counting information that is generated by using the converted positions, it is possible to reconstruct a highly fine PET image.

The scintillator 141 is configured monolithically. For this reason, no reflective material is interposed in the scintillator 141. As a result, the detector module 140 according to the first embodiment needs no calibration on the scintillator 141.

Furthermore, designing the detector module 140 is easy and each of the detector modules 140 has independency. For this reason, it is possible to design the detector 14 highly freely. The detector 14 may be assembled in various forms in addition to the form surrounding the subject P circularly.

Modification of First Embodiment

The above-described embodiment has been described as one where the system control circuitry 27 acquires the third intensity distributions and the fourth intensity distributions with respect to the representative position and determines the first intensity distribution; however, the embodiments are not limited thereto. For example, after determining the first intensity distributions with respect to representative positions, the system control circuitry 27 may further determine a first intensity distribution with respect to a position other than the representative position by function interpolation. In other words, the system control circuitry 27 performs function interpolation on the first intensity distributions with respect to multiple positions and calculates a first intensity distribution with respect to another position in the scintillator. For example, the system control circuitry 27 determines a first intensity distribution with respect to P12 that is an intermediate point between P1 and P2 illustrated in FIG. 9 as an average between the first intensity distribution with respect to P1 and the first intensity distribution with respect to P2.

Furthermore, the above-described embodiment is described as one where the counting information collection circuitry 15 specifies the first intensity distribution approximately identical with the second intensity distribution and specifies the conversion position; however, the embodiments are not limited thereto. For example, when the number of representative positions, which is set, is small, there may be no first intensity distribution approximately identical with the second intensity distribution. In this case, the counting information collection circuitry 15 calculates similarity between the first intensity distributions and the second intensity distribution and performs summing and averaging on the multiple positions by using the calculated similarity as a weight to specify the conversion position.

Other Embodiments

The embodiments are not limited to the above-described ones.

The above-described embodiment has been described as one where the detector module 140 includes the counting information calculation circuitry 143; however, the embodiments are not limited thereto. For example, the counting information calculation circuitry 143 may be provided independently of the detector module 140. Furthermore, the detector modules 140 may be sectioned into multiple blocks and each of the blocks may include the counting information calculation circuitry 143.

In the above-described embodiment, the counting information collection circuitry 15 is described as one that collects the signal processing results that are output by the respective counting information calculation circuitry 143; however, the embodiments are not limited thereto. For example, the counting information calculation circuitry 143 may output the signals from the SiPM panels 142 to the counting information collection circuitry 15 and the counting information collection circuitry 15 may process the signals from the respective SiPM panels 142. In this case, the counting information collection circuitry 15 collects the signals from the respective SiPM panels 142 and generates an intensity distribution indicating the intensities of the electric signals that are output by the respective SiPMs.

Furthermore, the above-described embodiment has been described as one where the correspondence information stored in the correspondence information storage circuitry 24d is generated by the system control circuitry 27; however, the embodiments are not limited thereto. For example, the counting information collection circuit 15 may execute the process of generating correspondence information. Furthermore, when correspondence information is generated, the electric signals that are output from the respective SiPMs may be collected by using the scintillators 141 contained in any one of the detector modules 140 in the detector 14 or may be collected outside the detector 14 by using the same scintillator as the scintillator 141 contained in the detector 14. Note that, when the electric signals are collected outside the detector 14, SiPM panels al in number to the channels of the detector module 140 in the detector 14 are used.

The above-described embodiment illustrates the case where, when correspondence information is generated, the first direction and the second direction are directions each perpendicular to the scintillator 141; however, the embodiments are not limited thereto. For example, if it is possible to determine a set of coordinates of the intersection between the first direction and the second direction, the first direction and the second direction need not be perpendicular to the scintillator 141.

In the above-described embodiment, the detector module 140 may include a light guide. In this case, the light guide transmits the scintillation light that is output from the scintillator 141 to the SiPM panels 142. The light guide is formed of, for example, a plastic material having excellent light transmittance.

In the above-described embodiment, the scintillator 141 is described as one having the shape of a hexahedron; however, the embodiments are not limited thereto. For example, the scintillator 141 may have the shape of a sphere. In that case, the SiPM panels 142 are arranged on different tangent planes of the scintillator 141 having the shape of a sphere. For example, the SiPM panels 142 are arranged on the tangents of the continuous respective points in the spherical shape, thereby being arranged along the spherical shape of the scintillator 141. When the SiPM panels 142 are arranged along the spherical shape of the scintillator 141, the SiPM panels 142 along the spherical shape are arranged in at least two parts in the scintillator 141. The SiPM panels 142 may be created along the spherical shape of the scintillator 141, thereby being arranged along the spherical shape of the scintillator 141. Alternatively, for example, the space may be filled with a light guide to form the spherical scintillator 141 into the shape of a hexahedron and the SiPM panels 142 may be provided on at least two faces of the scintillator 141.

The above-described embodiment illustrates the PET apparatus 100 as an exemplary nuclear medicine diagnostic apparatus; however, the embodiments are not limited thereto. For example, the nuclear medicine diagnostic apparatus may be a single photon emission computed tomography (SPECT) apparatus. Alternatively, the PET apparatus 100 may be one for breasts.

The word "processor" used in the descriptions given above refers to, for example, a central processing unit (CPU), a graphics processing unit (GPU) or may be an application specific integrated circuit (ASIC) or a programmable logic device (such as a simple programmable logic device (SPLD), a complex programmable logic device (CPLD) or a field programmable gate array (FPGA)). The processor implements functions by reading and executing a program that is saved in a storage circuit. Instead of saving the program in the storage circuit, the processor may be configured to have a circuit in which the program is directly incorporated. In this case, the functions are implemented by reading and executing the program that is incorporated in the circuit. Each processor of the embodiment is not limited to the case where each processor is configured as a single circuit. Multiple independent circuits may be combined into one processor to implement the functions. Furthermore, the multiple components illustrated in FIG. 1 may be integrated into a single processor and implement the functions.

In the descriptions of the above-described embodiments, each of the components of each of the devices illustrated in the drawings is a functional idea and is not necessarily configured physically as unillustrated in the drawings. In other words, specific modes of distribution and integration of the devices are not limited to those illustrated in the drawings. All or part of the devices may be configured in a distributed or integrated manner functionally or physically in any unit according to various types of loads and the situation in which the devices are used. Furthermore, all or part of the processing functions performed by the devices may be implemented by a CPU and a program that is analyzed and executed by the CPU or may be implemented as hardware based on a wired logic.

Furthermore, it is possible to implement the control method of the above-described embodiment by executing a control program prepared in advance with a computer, such as a personal computer or a work station. The control program may be distributed via a network, such as the Internet. The control program may be recorded in a computer-readable recording medium, such as a hard dish, a flexible disk (FD), a CD-ROM, a MO or a DVD, and may be read by the computer and thus executed.

According to at least one of the above-described embodiments, it is possible to specify an accurate position in which a gamma ray is converted into scintillation light.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nuclear medicine diagnostic apparatus, comprising:
  a scintillator formed of a single crystal and configured to convert a gamma ray into light;
  a plurality of photodetectors arranged on a plurality of different faces or tangents of the scintillator, each photodetector being configured to output an electric signal in response to incidence of the light resulting from the converting by the scintillator;
  a memory to store, in advance, three-dimensional correspondence information in which each three-dimensional position in the scintillator is associated with a corresponding first intensity distribution indicating intensities of the electric signals output by the respective photodetectors; and
  circuitry configured to determine a three-dimensional conversion position in which the gamma ray, which is emitted from a subject, is converted into the light in the scintillator by using the three-dimensional correspondence information and a second intensity distribution, the second intensity distribution indicating the intensities of the electric signals output by the respective photodetectors that detect the light originating from the gamma ray emitted from the subject and converted in the scintillator.

2. The nuclear medicine diagnostic apparatus according to claim 1, further comprising calculation circuitry configured to calculate first intensity distributions, each of which corresponds to one of a plurality of the positions, and store the first intensity distributions in the memory.

3. The nuclear medicine diagnostic apparatus according to claim 2, wherein the calculation circuitry is further configured to calculate an intensity distribution that is approximately identical between third intensity distributions, each indicating the intensities of the light incident on the scintillator from a first direction, and fourth intensity distributions, each indicating the intensities of the light incident on the scintillator from a second direction different from the first direction as the first intensity distribution with respect to a position that is an intersection between the first direction and the second direction.

4. The nuclear medicine diagnostic apparatus according to claim 3, wherein the calculation circuitry is further configured to calculate the first intensity distribution with respect to another position in the scintillator by performing function interpolation on the first intensity distributions with respect to the plurality of positions.

5. The nuclear medicine diagnostic apparatus according to claim 1, wherein the circuitry is further configured to calculate similarity between the first intensity distributions and the second intensity distribution and, based on the calculated similarity, determine the three-dimensional conversion position.

6. The nuclear medicine diagnostic apparatus according to claim 5, wherein the circuitry is further configured to use the calculated similarity as a weight, sum and average the plurality of positions, and determine the three-dimensional conversion position.

7. The nuclear medicine diagnostic apparatus according to claim 1, wherein the circuitry is further configured to further determine a time of the converting into the light by the scintillator based on a distance from the three-dimensional conversion position to the photodetector.

8. The nuclear medicine diagnostic apparatus according to claim 7, wherein the circuitry is further configured to correct the time based on the determined three-dimensional conversion position and a refractive index of the scintillator.

9. The nuclear medicine diagnostic apparatus according to claim 1, wherein the circuitry is further configured to determine an energy value of the gamma ray resulting from the converting into the light in the scintillator based on an amount of attenuation from the three-dimensional conversion position to the photodetector.

10. The nuclear medicine diagnostic apparatus according to claim 1, further comprising reconstruction circuitry configured to reconstruct an image from counting information generated by using the three-dimensional conversion position.

11. The nuclear medicine diagnostic apparatus according to claim 1, wherein the scintillator is a single crystal of any one of a rectangular cuboid and a cube.

12. A calibration method, comprising:
  storing, in a memory in advance, three-dimensional correspondence information in which each three-dimensional position in a scintillator, formed of a single crystal and configured to convert a gamma ray into light, is associated with a first intensity distribution indicating intensities of electric signals respectively output by a plurality of photodetectors arranged on a plurality of different faces or tangents of the scintillator, each photodetector being configured to output an electric signal in response to incidence of the light resulting from the converting by the scintillator; and
  determining, by using the three-dimensional correspondence information and a second intensity distribution indicating the intensities of the electric signals output by the respective photodetectors that detect the light originating from the gamma ray emitted from a subject and converted in the scintillator, a three-dimensional conversion position in which the gamma ray emitted from the subject is converted into the light in the scintillator.

13. The calibration method according to claim 12, further comprising calculating first intensity distributions, each of which corresponds to one of a plurality of the positions, and storing the first intensity distributions in the memory.

14. The calibration method according to claim 13, further comprising calculating an intensity distribution that is approximately identical between third intensity distributions each indicating the intensities of the light incident on the scintillator from a first direction, and fourth intensity distributions, each indicating the intensities of the light incident on the scintillator from a second direction different from the first direction as the first intensity distribution with respect to a position that is an intersection between the first direction and the second direction.

15. The calibration method according to claim 12, further comprising determining a time of the converting into the light by the scintillator based on a distance from the three-dimensional conversion position to the photodetector.

16. The calibration method according to claim 12, further comprising correcting the time based on the determined three-dimensional conversion position and a refractive index of the scintillator.

* * * * *